United States Patent [19]
Goldman

[11] Patent Number: 5,141,928
[45] Date of Patent: Aug. 25, 1992

[54] OPHTHALMIC MEDICATION

[76] Inventor: Lawrence Goldman, 19900 Beach Rd., Tequesta, Fla. 33469

[21] Appl. No.: 453,624

[22] Filed: Dec. 20, 1989

[51] Int. Cl.$^5$ .................... A61K 31/725; A61K 31/70
[52] U.S. Cl. ...................................... 514/54; 424/429; 514/56; 514/62; 514/839; 514/840; 514/912; 514/913; 514/914; 514/915
[58] Field of Search .................... 424/429; 514/54, 56, 514/62, 839, 840, 912, 913, 914, 915; 536/51, 54, 55.1

[56] References Cited

U.S. PATENT DOCUMENTS

| | | | |
|---|---|---|---|
| 3,710,796 | 1/1973 | Neefe | 424/429 |
| 4,489,065 | 12/1984 | Walton et al. | 536/54 |
| 4,500,519 | 2/1985 | Lormeau et al. | 514/56 |
| 4,524,066 | 6/1985 | Wolf | 536/118 |
| 4,692,435 | 9/1987 | Lormeau et al. | 514/56 |
| 4,699,900 | 10/1987 | Bayol et al. | 536/118 |
| 4,710,493 | 12/1987 | Landsberger | 514/56 |
| 4,713,373 | 12/1987 | Bayol et al. | 514/54 |
| 4,774,231 | 9/1988 | Petitou et al. | 536/118 |
| 4,812,448 | 3/1989 | Knepper | 514/913 |
| 4,814,437 | 3/1989 | de Belder et al. | 536/118 |
| 4,818,690 | 4/1989 | Pâques | 436/69 |
| 4,820,693 | 4/1989 | Gillespie | 514/56 |
| 4,826,826 | 5/1989 | Conti | 514/839 |
| 4,840,941 | 6/1989 | Ueno et al. | 536/20 |
| 4,861,760 | 8/1989 | Mazuel et al. | 514/915 |
| 4,870,166 | 9/1989 | Del Bono et al. | 536/54 |
| 4,885,361 | 12/1989 | Wessel | 536/118 |
| 4,908,354 | 3/1990 | Seidel et al. | 436/87 |
| 4,931,279 | 6/1990 | Bawa et al. | 424/429 |
| 4,966,894 | 10/1990 | Herr et al. | 514/56 |

OTHER PUBLICATIONS

The Merck Index, Tenth Edition, Published by Merck & Co., Inc., Rahway, N.J., U.S.A. 1983 pp. 890 & 891.

*Primary Examiner*—Ronald W. Griffin
*Attorney, Agent, or Firm*—Cooper & Dunham

[57] ABSTRACT

Glycosaminoglycan polysulfates (GAGPS) have been found to be useful in ophthalmic medications in the prevention and treatment of eye injuries. Particularly useful are GAGPS having a molecular weight in the range of 5,000–20,000 daltons. GAGPS-containing ophthalmic medications are usefully combined with an antibiotic in the treatment of ocular fungal or bacterial infections or with an antibiotic in the treatment of fungal or bacteria infections or with an anti-glaucoma agent, such as pilocarpine or epinephrine, in the treatment of glaucoma. Also, of particular usefulness are GAGPS solutions or dispersions used to enhance healing after corneal abrasion or surgical insult.

12 Claims, No Drawings

OPHTHALMIC MEDICATION

BACKGROUND OF THE INVENTION

Glycosaminoglycan polysulfates (GAGPS) are one of a group of linear heteropolysaccharides, e.g. chondroitin sulfate, dermatan sulfate, keratan sulfate, heparin sulfate, heparin and hyaluronic acid, that contain hexosamines and occur both as components of proteoglycans and as free compounds. The dissacharide repeating unit contains hexuronic acid, except for keratan sulfate, which contains galactose, N-acetylhexosamine sulfate and hyaluronic acid, which contain N-acetyl glucosamine. Such dissacharide repeating units are all glycosaminoglycan polysulfates except hyaluronic acid and keratan sulfate which contain carboxy (—COOH) and an acid sulfate (—SO$_3$H) (residue). Hyaluronic acid contains a —SO$_3$H residue per repeating unit. In water solutions at physiologic pH, all glycosaminoglycan polysulfates have many negative charges, producing electrostatic repulsion. This causes the molecules to spread through a large volume of solvent, forming a highly viscous fluid. GAGPS were formally called mucopolysaccharides, a name still in common chemical usage.

A number of techniques are known for the production of glycosaminoglycan polysulfates, see for example, U.S. Pat. No. 4,524,066. Therein it is disclosed that the GAGPS described therein have certain medical applications useful in humans including use as a thrombolytic agent, an antilipemic agent, an anti-inflammatory agent, an anti-arthritic agent, an anti-athrosclerotic agent and as a virustatic agent, The disclosures of U.S. Pat. No. 4,524,066 are herein incorporated and made part of this disclosure.

SUMMARY OF THE INVENTION

It has now been discovered that glycosaminoglycan polysulfates (GAGPS) are useful in ophthalmic or eye medications and related materials and uses in the prevention or treatment of various eye conditions and injuries. Preferably, the molecular weight of GAGPS employed in such medications has a fairly low molecular weight, about 5,000 daltons, preferably in the range form about 5,000 to about 20,000 daltons, more or less. GAGPS in such ophthalmic or eye medications is usually present in a minor effective amount 0.0001% to about 0.55% by weight, although other amounts or concentrations are usefully employed depending upon the condition being treated.

Preferably, the GAGPS-containing ophthalmic eye medications are in aqueous liquid form suitable for use as eye drops. Aqueous gel and non-aqueous and particulate composition, (such as sterile dispersions in petrolatum) including solid formulations useful for insertion into or onto the eye, containing GAGPS are also useful. In addition to GAGPS there may be also included in the GAGPS-containing compositions an antibiotic, such as a cephalosporin, a penicillin, a tetracycline or an antiglaucoma agent, such as pilocarpine or epinephrine. Additionally, there may be included in the GAGPS-containing ophthalmic medications other medications or adjuvants, such as enzyme inhibitors, such as acetazolamide (Diamox), together with a preservative, such as E.D.T.A. benzalkonium chloride, mercural thimerosol, along with other medications including steroids, hormones, etc. depending upon the purpose of the GAGPS-containing compositions or the eye conditions to be treated.

DETAILED DESCRIPTION OF THE INVENTION

The glycosaminoglycan polysulfates which have a molecular weight of above about 5,000 daltons, such as in the range 5,000-20,000, more or less, are particularly useful in accordance with the practices of this invention. In the prevention and treatment of ocular diseases a particular characteristic of GAGPS which makes GAGPS-containing materials suitable for prevention and treatment of ocular diseases, resides in the apparent capabilities of GAGPS to adhere to tissue. Also, GAGPS exhibit anti-enzyme activity or the ability to inhibit enzyme activity, such as proteolytic enzyme activity and lysosomal enzyme activity.

There are two physiological areas of interest in preventing or treating ocular diseases employing GAGPS in accordance with the practices of this invention. The first such area could be considered as superficial or corneal/pre-corneal. In the practices of the invention with respect to this aspect, one would look to or employ agents or compounds in addition to or including GAGPS which would have a beneficial effect on the intact or abraded cornea, as GAGPS appears to possess. Such disease entities usefully treated with GAGPS include superficial corneal infections, karatoconjunctivitis sicca, karatoconjunctivitis filiformis, pemphigus and symblepharon.

The other physiological area of interest in the practices of this invention and wherein GAGPS is usefully employed is sub-corneal, i.e. behind the corneal surface. The most important sub-corneal disease entity presently contemplated and which is treated topically and systemically is glaucoma. Glaucoma involves a condition wherein excess fluid is excreted from the aqueous humour without an adequate passage or exit. As a consequence of this fluid buildup, there is an increase in intraocular pressure, ultimately causing a gradual loss of peripheral vision. In time, vision becomes narrower and narrower to so-called tunnel vision, and ultimately blindness. This ultimate condition is the direct result of the progressive degeneration of the optic nerve.

As mentioned hereinabove, GAGPS appears to bond or adhere selectively to tissue, particularly cartilage, and it is pointed out that cartilage is closely related to corneal tissue. Both such tissues, cartilage and corneal, are derived philogenetically from the mesenchyme. Upon application of GAGPS, therefore, one would expect to find GAGPS adhering to and in contact with such tissue. The simplest method of applying GAGPS to the eye, therefore, would be through eye drops whereby GAGPS is brought directly into contact with the eye with resulting selective adherence of GAGPS to the corneal tissue.

Although GAGPS alone would appear to be useful in the prevention and treatment of ocular diseases, particularly bacterial, viral and/or fungal infections and the like, because of the selective adherence of GAGPS to the eye tissue with resulting interference with and/or displacement of bacterial and/or other infectious agents therefrom, it would be useful in accordance with the practices of this invention in the prevention and treatment of ocular diseases, as indicated hereinabove, to employ, GAGPS compositions, preferably in the form of eye drops, which would contain both GAGPS and a suitable antibiotic and/or, if desirable, anti-fungal agent or other adjuvant including other materials having a medicational effect or other therapeutic or other desirable physiological properties, such as steroids and hormones.

Suitable such antibiotic agents usefully employed in combination with GAGPS in accordance with the practices of this invention including penicillin, streptomycin, cephalosporin, tetracycline, chloramphenicol, and antibacterial substituted quinoline carboxylic acids, such as norfloxacin and ciprofloxacin, the steroids, such as prednisone, and other well known ophthmalic or ocular medications including hormones. These other agents, antibacterial or otherwise, such as anti-glaucoma agents, e.g. Betadine, are usefully combined with GAGPS in the preparation of compositions suitable for and useful for the treatment of bacterial and the like ocular infections and/or eye conditions, including glaucoma.

In the preparation of GAGPS compositions in accordance with this invention useful for the prevention and treatment of ocular diseases and the like, including corneal abnormalities, and in order to gain penetration through the cornea for the treatment of conditions, such as glaucoma, one would include, as indicated, along with GAGPS an adjuvant which desirably would be soluble in both aqueous and lipid phases. Since GAGPS is polyanionic, GAGPS does not meet these criteria. However, the combination of GAGPS with well known anti-glaucoma agents, such as pilocarpine and epinephrine, would be useful in accordance with the practices of this invention for the treatment of glaucoma. Accordingly, the combination of an anti-glaucoma agent, such as pilocarpine, and GAGPS in eyedrop compositions in accordance with this invention or other well known anti-glaucoma agents in combination with GAGPS, would be usefully employed in the treatment of glaucoma, Since GAGPS selectively and strongly adheres to corneal tissue surfaces, it would serve to maintain the effective anti-glaucoma agent, such as pilocarpine, within the eye and in contact with the corneal surface for a longer and effective period of time.

As mentioned hereinabove, GAGPS possesses anti-enzymatic properties, particularly as inhibitors of proteolytic enzymes and lysosomal enzymes. This anti-proteolytic enzyme activity possessed by GAGPS would be particularly useful in preventing bacterial damage to the cornea which might have been injured by trauma, such as by an ill-fitting contact lens, or during surgery, In general, GAGPS in accordance with this invention serves to promote corneal wound healing and prevent infections. Accordingly, the application of GAGPS to a corneal wound or after corneal surgery would serve to promote healing, particularly where intraocular lenses are inserted, would be a particular effective and useful application of this invention in that GAGPS would improve the corneal healing process. Also, the use of GAGPS in the treatment and/or prevention of corneal abrasions due to accident or because of the wearing of improper, ill-fitting lenses is a very important and significant use and application of the practices of this invention. Once a cornea loses its integrity, it is susceptible to many infectious processes which an ordinary intact cornea effectively manages. Therefore, an agent, such as GAGPS, which helps to restore corneal integrity and prevent infections and proteolytic enzyme damage would be of great value and utility in the field of ophthalmic medications.

Further, as mentioned hereinabove, GAGPS ophthalmic compositions or solutions in accordance with this invention also have a beneficial effect in the treatment of filiform keratitis. This, therefore, indicates the wide applicability and utility of GAGPS in ophthalmic medications and its use in the prevention and treatment of ocular diseases and injuries. As mentioned hereinabove, GAGPS appear to be effective as an ophthalmic medications because of its strong adherence to tissue, particularly corneal and ocular tissue, and tends to preferably occupy sites which might be occupied by and otherwise displace infectious bacteria, such as gram-negative and gram-positive bacteria, particularly in the absence of fibronectin. Accordingly, GAGPS would be effective in the prevention and treatment of ocular diseases and infections in the sense that they displace bacterial and other infectious or irritant bodies or agents and displace and remove the same.

This aspect of GAGPS accordingly is particularly useful for the preparation of compositions or liquid baths for the storage of hard or soft, contact lenses, especially the socalled soft, hydratable, permeable contact lenses, contact lenses which are oxygen permeable, such as the hydroxy ethylmethacrylate contact lenses Even the non-hydrated or non-hydratable lenses, including the hydrophobic silicone lenses, are also usefully stored and maintained prior to use in solutions in accordance with this invention which contain GAGPS, preferably together with an antibiotic or antibacterial agent as mentioned hereinabove and desirably also, if necessary, a preservative, such as E.D.T.A. or mercurial thimerosal. One interesting aspect of the practices of this invention would be to coat or otherwise impregnate or incorporate contact lenses, particularly the soft contact lenses, the oxygen-permeable hydratable lenses, e.g. the soft hydroxy ethylmethacrylate lenses, with GAGPS. The lens would be coated or impregnated or soaked in a GAGPS solution before insertion into the eye, thereby providing a better protection for the eye against infection and/or serving as a medication to the eye for the treatment of an ocular bacterial infection and for the other purposes for which GAGPS is useful as described hereinabove.

GAGPS-containing compositions in accordance with this invention which are useful as ophthalmic medications for the treatment of human or animal ocular diseases include aqueous GAGPS solutions which might also include other materials, such as antibiotics, steroids, hormones, adjuvants and the like. Suitable such compositions are:

EXAMPLE NO. 1

An aqueous liquid composition useful for application to the eye as an eyedrop containing 0.1-1.0% by weight GAGPS having a molecular weight in the range 6.000-10,000 daltons in a suitable physiologically acceptable aqueous carrier.

EXAMPLE NO. 2

An aqueous liquid GAGPS-containing composition suitable for application to the eye in the form of eye drops containing GAGPS in an amount in the range 0.01-0.5% GAGPS having a molecular weight in the range 5,000-20,000 daltons, together with an antibiotic.

EXAMPLE NO. 3

An aqueous gel composition suitable for direct application to the eye consisting essentially of an aqueous gelling agent and 0.2-0.8% by weight GAGPS having a molecular weight in the range 8,000-10,000 daltons.

EXAMPLE NO. 4

An ophthalmic composition useful as a form of eye drops for the treatment of glaucoma comprising an aqueous liquid composition containing 0.1-5.0% by weight GAGPS having a molecular weight in the range 5,000-20,000 daltons and an effective amount of anti-glaucoma agent, pilocarpine or other anti-glaucoma agent.

As will be apparent to those skilled in the art in the light of the foregoing disclosures, many modifications, alterations and substitutions are possible in the practices of this invention without departing from the spirit or scope thereof.

What is claimed is:

1. A method of treating eye infections which comprises applying to the eye an effective amount of a glycosaminoglycan polysulfate (GAGPS).

2. A method in accordance with claim 1 wherein said GAGPS has a molecular weight in the range from about 5,000 to about 20,000 daltons.

3. A method of treating eye infections which comprises applying to the eye an effective amount of a composition comprising glycosaminoglycan polysulfate (GAGPS) and a medication selected from the group consisting of anti-glaucoma agents and antimicrobial or antibiotic agents.

4. A method of treating or storing an eye contact lens which comprises immersing said lens or placing said lens in contact with a liquid aqueous solution containing a minor amount of a glycosaminoglycan polysulfate (GAGPS).

5. A method in accordance with claim 4 wherein said aqueous solution additionally contains a preservative.

6. A method of inhibiting proteolytic enzyme activity in the eye which comprises applying to or contacting the eye with an effective proteolytic enzyme inhibiting amount of glycosaminoglycan polysulfate (GAGPS).

7. A method in accordance with claim 6 wherein said GAGPS has a molecular weight in the range from about 5,000 to about 20,000 daltons.

8. A method of treating the eye to promote corneal wound healing which comprises applying to or contacting the eye with an effective amount of a glycosaminoglycan polysulfate 9. A method of healing a damaged cornea which comprises applying to the eye an effective amount of a glycosaminoglycan polysulfate (GAGPS).

10. A method of treating a person after cataract surgery involving the removal of a cataract so as to speed corneal healing which comprises administering to the eye after cataract removal an effective amount of a glycosaminoglycan polysulfate (GAGPS).

11. A method of speeding up corneal healing or preventing corneal injury or restoring corneal integrity which comprises applying to the eye an effective amount of glycosaminoglycan polysulfate (GAGPS).

12. A method of treating eye infections or ocular diseases which comprises directly apply to the eye a sterile dispersion or solution of glycosaminoglycan polysulfate (GAGPS), said GAGPS having a molecular weight in the range from about 5,000 to about 20,000 daltons.

* * * * *

REEXAMINATION CERTIFICATE (2732th)

United States Patent [19]

Goldman

[11] B1 5,141,928

[45] Certificate Issued  Nov. 14, 1995

[54] OPHTHALMIC MEDICATION

[75] Inventor: Lawrence Goldman, Tequesta, Fla.

[73] Assignee: Brujo Incorporated, Austin, Tex.

Reexamination Request:
No. 90/003,390, Apr. 5, 1994

Reexamination Certificate for:
Patent No.: 5,141,928
Issued: Aug. 25, 1992
Appl. No.: 453,624
Filed: Dec. 20, 1989

[51] Int. Cl.$^6$ .......................... A61K 31/725; A61K 31/70
[52] U.S. Cl. .................. 514/54; 424/429; 514/56; 514/62; 514/839; 514/840; 514/912; 514/913; 514/914; 514/915
[58] Field of Search ............... 514/54, 56, 62, 514/839, 840, 912, 913, 914, 915; 424/429; 536/51, 54, 55.1

[56] References Cited

U.S. PATENT DOCUMENTS

| | | | |
|---|---|---|---|
| 3,710,796 | 1/1973 | Neefe | 424/429 |
| 4,365,050 | 12/1982 | Ivani | 536/53 |
| 4,489,065 | 12/1984 | Walton et al. | 536/54 |
| 4,500,519 | 2/1985 | Lormeau et al. | 514/56 |
| 4,524,066 | 6/1985 | Wolf | 536/118 |
| 4,692,435 | 9/1987 | Lormeau et al. | 514/56 |
| 4,696,917 | 9/1987 | Lindstrom et al. | 514/54 |
| 4,699,900 | 10/1987 | Bayol et al. | 536/118 |
| 4,710,493 | 12/1987 | Landsberger | 514/56 |
| 4,713,373 | 12/1987 | Bayol et al. | 514/54 |
| 4,774,231 | 9/1988 | Petitou et al. | 536/118 |
| 4,812,448 | 3/1989 | Knepper | 514/913 |
| 4,814,437 | 3/1989 | de Belder et al. | 536/118 |
| 4,818,690 | 4/1989 | Pâques | 436/69 |
| 4,820,693 | 4/1989 | Gillespie | 514/56 |
| 4,826,826 | 5/1989 | Conti | 514/839 |
| 4,840,941 | 6/1989 | Ueno et al. | 536/20 |
| 4,861,760 | 8/1989 | Mazuel et al. | 514/915 |
| 4,870,166 | 9/1989 | Del Bono et al. | 536/54 |
| 4,885,361 | 2/1989 | Wessel | 536/118 |
| 4,886,786 | 12/1989 | Lindstrom et al. | 514/54 |
| 4,908,354 | 3/1990 | Seidel et al. | 436/87 |
| 4,931,279 | 6/1990 | Bawa et al. | 424/429 |
| 4,966,894 | 10/1990 | Herr et al. | 514/56 |
| 5,141,928 | 8/1992 | Goldman | 514/54 |

FOREIGN PATENT DOCUMENTS

| | | |
|---|---|---|
| 63973A1 | 11/1982 | European Pat. Off. . |
| 138572 | 4/1985 | European Pat. Off. . |
| 197718 | 10/1986 | European Pat. Off. . |
| 208623 | 1/1987 | European Pat. Off. . |
| 2207049 | 1/1989 | United Kingdom . |

OTHER PUBLICATIONS

The Merck Index, Tenth Edition, Published By Merck & Co., Inc., Rahway, N.J., U.S.A. 1983 pp. 890 & 891.

Iwata et al., "Studies on the biocompatibility of contact lens materials. III. The effects of viscous agents cell adhesion to lens materials.", *Chemical Abstracts*, vol. 96, No. 16, Apr. 19, 1982, p. 461, col. 2, Abstract No. 129739j. Nippon Kontakuto Renzu Gakkai Kaishi, 1981, 23(3): 181 (Japan) (1981).

Gurney et al., "Design and Evaluation of Controlled Release Systems for the Eye," *Chemical Abstracts*, 108, No. 12, Abstract No. 101212z, *J. Controlled Release*, 6:367, (1987).

Ismail et al, "Ocular Effects of the Venom From the Spitting Cobra (*Naja nigricollis*)," *Clin. Toxicol*, 24:183–202 (1986).

Greiling, et al., "Inhibition of Lysosomal Enzymes by a Glycosaminoglycan Polysulfate, Arnzeimittel–Forschung," 23:593–597 (1973).

*Primary Examiner*—Ronald W. Griffin

[57] ABSTRACT

Glycosaminoglycan polysulfates (GAGPS) have been found to be useful in ophthalmic medications in the prevention and treatment of eye injuries. Particularly useful are GAGPS having a molecular weight in the range of 5,000–20,000 daltons. GAGPS-containing ophthalmic medications are usefully combined with an antibiotic in the treatment of ocular fungal or bacterial infections or with an antibiotic in the treatment of fungal or bacteria infections or with an anti-glaucoma agent, such as pilocarpine or epinephrine, in the treatment of glaucoma. Also, of particular usefulness are GAGPS solutions or dispersions used to enhance healing after corneal abrasion or surgical insult.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–12 are cancelled.

New claims 13–26 are added and determined to be patentable.

13. A method of treating an eye infection which comprises applying to the eye an amount of a glycosaminoglycan polysulfate (GAGPS) composition effective to treat the eye infection, the glycosaminoglycan polysulfate (GAGPS) being selected from the group consisting of dermatan sulfate, keratan sulfate and chondroitin sulfate, wherein the chondroitin sulfate has a molecular weight up to about 15,000.

14. The method of claim 13, wherein the dermatan sulfate or keratan sulfate has a molecular weight in the range from about 5,000 to about 20,0000 Daltons.

15. The method of claim 13, wherein the GAGPS composition further comprises a medication selected from the group consisting of an antimicrobial agent, an antibiotic agent, and an antifungal agent.

16. A method of treating or storing an eye contact lens comprising the step of contacting the eye contact lens with a glycosaminoglycan polysulfate (GAGPS) composition selected from the group consisting of dermatan sulfate, keratan sulfate and chondroitin sulfate, wherein the chondroitin sulfate has a molecular weight up to about 15,000.

17. The method of claim 16, wherein the GAGPS composition further comprises a preservative.

18. The method of claim 16, wherein the dermatan sulfate or keratan sulfate has a molecular weight in the range from about 5,000 to about 20,000 Daltons.

19. A method of inhibiting proteolytic enzyme activity in an eye comprising the step of applying to the eye an amount of a glycosaminoglycan polysulfate (GAGPS) composition effective to inhibit proteolytic enzyme activity in the eye, the glycosaminoglycan polysulfate (GAGPS) being selected from the group consisting of dermatan sulfate, keratan sulfate and chondroitin sulfate, wherein the chondroitin sulfate has a molecular weight up to about 15,000.

20. The method of claim 19, wherein the dermatan sulfate or keratan sulfate has a molecular weight in the range from about 5,000 to about 20,000 Daltons.

21. A method of promoting corneal healing of a damaged cornea comprising the step of applying to the damaged cornea an amount of a glycosaminoglycan polysulfate (GAGPS) composition effective to promote corneal healing, the glycosaminoglycan polysulfate (GAGPS) being selected from the group consisting of dermatan sulfate, keratan sulfate and chondroitin sulfate, wherein the chondroitin sulfate has a molecular weight up to about 15,000.

22. The method of claim 21, wherein the dermatan sulfate or keratan sulfate has a molecular weight in the range from about 5,000 to about 20,000 Daltons.

23. A method of treating an eye after cataract removal comprising the step of applying to the eye after cataract removal an amount of a glycosaminoglycan polysulfate (GAGPS) composition effective to treat the eye after cataract removal, the glycosaminoglycan polysulfate (GAGPS) being selected from the group consisting of dermatan sulfate, keratan sulfate and chondroitin sulfate, wherein the chondroitin sulfate has a molecular weight up to about 15,000.

24. The method of claim 23, wherein the dermatan sulfate or keratan sulfate has a molecular weight in the range from about 5,000 to about 20,000 Daltons.

25. A method of treating glaucoma comprising applying to an eye with glaucoma an amount of a glycosaminoglycan polysulfate (GAGPS) composition effective to treat the glaucoma, the glycosaminoglycan polysulfate (GAGPS) being selected from the group consisting of dermatan sulfate, keratan sulfate and chondroitin sulfate, wherein the chondroitin sulfate has a molecular weight up to about 15,000.

26. The method of claim 25, wherein the dermatan sulfate or keratan sulfate has a molecular weight in the range from about 5,000 to about 20,000 Daltons.

* * * * *